United States Patent
Nakanishi et al.

(10) Patent No.: US 8,517,952 B2
(45) Date of Patent: Aug. 27, 2013

(54) BLOOD PRESSURE MONITOR

(75) Inventors: Takashi Nakanishi, Nishitokyo (JP);
Kenichi Matsumoto, Nishitokyo (JP);
Takuro Kohyama, Nishitokyo (JP)

(73) Assignee: Citizen Holdings Co., Ltd., Tokyo (JP)

( * ) Notice: Subject to any disclaimer, the term of this patent is extended or adjusted under 35 U.S.C. 154(b) by 789 days.

(21) Appl. No.: 12/450,398

(22) PCT Filed: Mar. 24, 2008

(86) PCT No.: PCT/JP2008/055356
§ 371 (c)(1),
(2), (4) Date: Sep. 24, 2009

(87) PCT Pub. No.: WO2008/123167
PCT Pub. Date: Oct. 16, 2008

(65) Prior Publication Data
US 2010/0121205 A1    May 13, 2010

(30) Foreign Application Priority Data
Mar. 30, 2007   (JP) .................................. 2007-093013

(51) Int. Cl.
*A61B 5/02* (2006.01)
(52) U.S. Cl.
USPC ........... 600/499; 600/485; 600/490; 600/493; 600/494; 600/500

(58) Field of Classification Search
USPC ................. 600/485, 490, 493, 500–502, 499; 606/201–203
See application file for complete search history.

(56) References Cited

U.S. PATENT DOCUMENTS

| | | | |
|---|---|---|---|
| 4,206,765 A * | 6/1980 | Huber | ........................... 600/490 |
| 4,465,076 A * | 8/1984 | Sturgeon | ....................... 600/499 |
| 5,323,782 A | 6/1994 | Shirasaki et al. | |
| 7,070,567 B2 | 7/2006 | Mizukoshi et al. | |

FOREIGN PATENT DOCUMENTS

| | | |
|---|---|---|
| JP | S61-130203 U | 8/1986 |
| JP | H01-256930 A | 10/1989 |
| JP | H02-37604 U | 3/1990 |
| JP | H05-095920 A | 4/1993 |
| WO | WO 2006079593 A1 * | 8/2006 |

\* cited by examiner

*Primary Examiner* — Patricia Mallari
*Assistant Examiner* — Christian Jang
(74) *Attorney, Agent, or Firm* — Manabu Kanesaka (57) ABSTRACT

It is an object to provide a blood pressure monitor, wherein the noise caused by the friction of overlapping parts of a cuff can be inhibited during automatic elevation in the cuff pressure, and reliability in the automatic elevation of cuff pressure can be significantly enhanced.

A cuff (1) is used in a blood pressure monitor to measure a blood pressure in a rolled condition where one end of the cuff (1) is wound within the other end thereof, wherein a cushion member (6) made of a raised fabric (61) is provided in at least one of surfaces at one end and the other end of the cuff (1) which rub against each other.

10 Claims, 6 Drawing Sheets

BLOOD PRESSURE MONITOR

TECHNICAL FIELD

The present invention relates to a blood pressure monitor. More particularly, the present invention relates to a blood pressure monitor which is used for an automatic blood pressure monitor and which includes noise generation inhibiting means for inhibiting the noise caused by the friction of overlapping parts of a cuff to elevate a cuff pressure to a proper pressure value.

BACKGROUND ART

Recently, blood pressure monitors have come into wide use in, for example, not only hospitals but also general households for the purpose of health care. The blood pressure monitors for the general households are typically automatic blood pressure monitors that are easy to operate.

Automatic blood pressure monitors based on various measurement methods and configurations have been developed, and an oscillometric electronic blood pressure monitor is one of such blood pressure monitors. This oscillometric electronic blood pressure monitor detects a pulse wave superposed on cuff pressure, and calculates a blood pressure on the basis of changes in the amplitude of the pulse wave.

Figure 5:
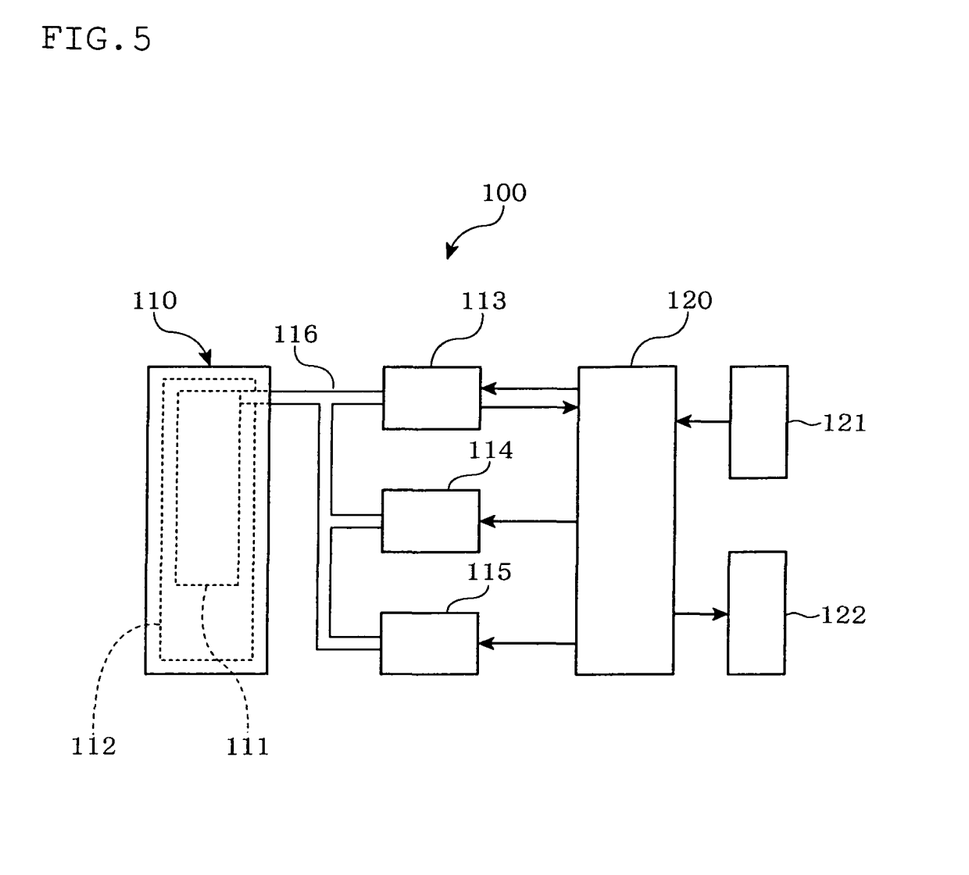
FIG. 5 shows a schematic block diagram of essential parts of a conventional oscillometric electronic blood pressure monitor.

As shown in FIG. 5, the above-mentioned oscillometric electronic blood pressure monitor 100 includes a cuff 110, a pressure sensor 113, a pump 114, an exhaust valve 115, an information processing unit 120, an operation switch 121 and a display 122. The cuff 110 has an air bag 111 and a core 112. The pressure sensor 113, the pump 114 and the exhaust valve 115 are in communication with the air bag 111 through a tube 116. The information processing unit 120 is connected to the pressure sensor 113, the pump 114 and the exhaust valve 115. The operation switch 121 and the display 122 are connected to the information processing unit 120.

During a blood pressure measurement, the cuff 110 is attached to the upper arm in a rolled condition where one end of the cuff is wound within the other end thereof. Further, a pressure signal is input to the information processing unit 120 from the pressure sensor 113 via a filter and an A/D converter (not shown), and the information processing unit 120 controls the pump 114 and the exhaust valve 115.

Figure 6:
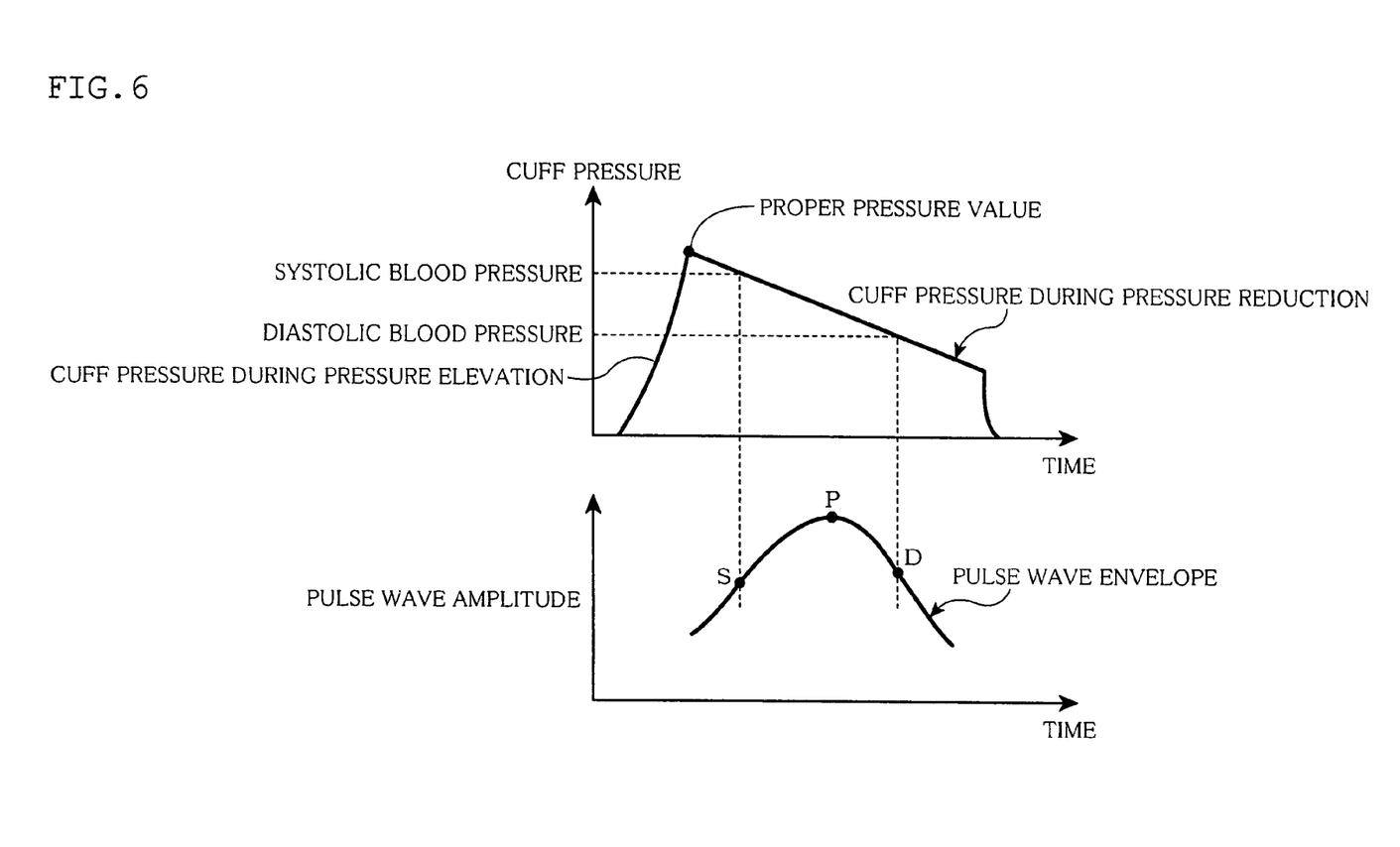
FIG. 6 shows a graph explaining cuff pressure and pulse wave amplitude in the conventional oscillometric electronic blood pressure monitor.

As shown in FIG. 6, in the oscillometric electronic blood pressure monitor 100, the cuff pressure is first elevated to a proper pressure value. Then, in the process of gradual reduction of the cuff pressure, the oscillometric electronic blood pressure monitor 100 measures a systolic blood pressure (maximum blood pressure) and a diastolic blood pressure (minimum blood pressure). At this moment, a change pattern (pulse wave envelope) of the pulse wave amplitude is required in an oscillometric method. This pulse wave envelope includes a point S corresponding to the systolic blood pressure, the maximum (point P) of the pulse wave amplitude and a point D corresponding to the diastolic blood pressure.

That is, the oscillometric electronic blood pressure monitor 100 has to previously elevate the pressure to the S point or more before the start of measurement operation. If the pressure is not elevated to the S point or more (elevation of the pressure to the proper pressure value), the S point is absent at the point of detection of the point P in the blood pressure measurement operation. In this case, the systolic blood pressure (maximum blood pressure) cannot be calculated, resulting in a measurement error.

Conventional Examples

Moreover, various techniques have been developed for the automatic blood pressure monitors.

For example, Patent document 1 discloses a technique for a method of automatically setting cuff pressure. According to this technique, a pulse wave signal is detected by a pressure sensor in the process of elevating the cuff pressure, a pulse wave having the maximum amplitude is detected from the pulse wave signal. A pressure in which a predetermined value is added to the cuff pressure at this moment is set as a proper pressure value, and the pressure of the cuff is elevated to this proper pressure value.

Another technique for an electronic blood pressure monitor is disclosed in Patent document 2. This electronic blood pressure monitor includes threshold value calculating means, judging means, maximum blood pressure estimating means and pressure setting means. The threshold value calculating means detects the maximum value of the amplitude of the pulse wave during the pressure elevation of the cuff, and figures out a threshold value on the basis of the maximum value. The judging means compares the threshold value calculated by the threshold value calculating means with the pulse wave amplitude during the pressure elevation, and judges whether the pulse wave amplitude during the pressure elevation is lower than the threshold value. The maximum blood pressure estimating means linearly complements the pulse wave amplitude at the point where the pulse wave amplitude during the pressure elevation is judged to be lower than the threshold value by the judging means. The maximum blood pressure estimating means sets a pressure value corresponding to the linearly complemented value as an estimated value of the maximum blood pressure. The pressure setting means stops the elevation of the cuff pressure at the point where the pressure value has elevated a predetermined pressure with respect to the value estimated by the maximum blood pressure estimating means.

Still another technique for a blood pressure measurement double cuff is disclosed in Patent document 3. This blood pressure measurement double cuff includes a vibration shielding plate provided between an avascularization bag and a pulse wave detecting bag. Between the vibration shielding plate and the pulse wave detecting bag, a slide cloth is provided to prevent the contact between the vibration shielding plate and the pulse wave detecting bag.

According to this technique, noise caused by the friction during a blood pressure measurement can be reduced.

Patent document 1: Japanese Patent Publication Laid-open No. 1-256930

Patent document 2: Japanese Patent No. 2842696

Patent document 3: Japanese Patent Publication Laid-open No. 2004-321251

DISCLOSURE OF THE INVENTION

Problems to be Solved by the Invention

The techniques described in above-mentioned Patent documents 1, 2 are intended to automatically elevate the cuff pressure to the proper pressure value. However, these techniques are based on the premise that a small pulse wave signal of a subject can be accurately detected from a pressure signal during pressure elevation. That is, when air is supplied to the air bag 111, the cuff 110 wound around the arm in a rolled condition where one end of the cuff is wound within the other end thereof tightens the arm, and at the same time, overlapping parts of the cuff 110 may rub against each other. This rubbing generally ranges over a small distance. The problem is that if noise caused by this rubbing is erroneously detected as a pulse wave signal, the cuff pressure cannot be automatically set any more or an erroneous cuff pressure is set.

Moreover, the technique described in Patent document 3 is a technique for reducing the noise caused by the friction during a blood pressure measurement in the blood pressure measurement double cuff. However, the problem of this technique is that the aforementioned problem cannot be effectively solved.

The present invention has been proposed to solve the problems of the conventional techniques described above. It is therefore an object of the present invention to provide a blood pressure monitor, wherein the noise caused by the friction of overlapping parts of a cuff can be inhibited during automatic elevation in the cuff pressure, and reliability in the automatic elevation of cuff pressure can be significantly enhanced.

Means for Solving the Problems

In order to achieve the foregoing object, the present invention provides a blood pressure monitor to measure a blood pressure in a rolled condition where one end of a cuff is wound within the other end thereof, which includes a tightening belt to diametrically reduce the cuff, wherein a cushion member is provided in an area, which is at least one of surfaces at one end and the other end of the cuff which rub against each other, where the tightening belt is overlapped.

Thus, the cuff is first tightened on an arm in a rolled condition by the tightening belt. Then, if air is sent into an air bag, one end and the other end of the cuff move away from each other due to the counteraction of force compressing the arm. At this moment, noise caused by the friction of overlapping parts of the cuff can be inhibited by the cushion member. Accordingly, reliability in the automatic elevation of cuff pressure can be significantly enhanced.

Preferably, the cushion member is made of a raised fabric.

Thus, the cushion member can be a simple and inexpensive member, thereby enabling a reduction in manufacturing costs.

In order to achieve the foregoing object, the present invention provides a blood pressure monitor to measure a blood pressure in a rolled condition where one end of a cuff is wound within the other end, which includes a tightening belt to diametrically reduce the cuff, wherein slide means is provided in an area, which is at least one of surfaces at one end and the other end of the cuff which rub against each other, where the tightening belt is overlapped.

Thus, the cuff is first tightened on an arm in a rolled condition by the tightening belt. Then, if air is sent into an air bag, one end and the other end of the cuff move away from each other due to the counteraction of force compressing the arm. At this moment, noise caused by the friction of overlapping parts of the cuff can be inhibited by the slide means because one end and the other end of the cuff slide without rubbing against each other. Accordingly, reliability in the automatic elevation of cuff pressure can be significantly enhanced.

Preferably, the slide means is provided in the vicinity of the tip of one end of the cuff, and/or in the vicinity of the tip of the other end of the cuff.

Thus, the slide means can be efficiently disposed at a place where there is great possibility of friction between parts of the cuff.

Preferably, the slide means has a rotary member which is in contact with at least one of one end and the other of the cuff and which is rotatable in a direction where the one end and the other end slide.

Thus, the one end and the other end of the cuff smoothly slide, and noise caused by friction can be effectively inhibited.

Preferably, the slide means has a shaft provided in a direction perpendicular to the direction where the one end and the other end of the cuff slide, the shaft being inserted in a through-hole formed in the rotary member.

Thus, the slide means can be simple in configuration, thereby enabling a reduction in manufacturing costs.

Moreover, both ends of the shaft are preferably stored between a core and a cover covering this core. This enables the shaft to be easily held without providing any particular bearing.

Preferably, the rotary member is a cylindrical member and/or a spherical member.

Thus, the contact area between the rotary member and the cuff is reduced, so that noise caused by friction can be further reduced.

Preferably, the slide means has a plurality of rotary members.

This further ensures that noise caused by friction can be reduced by the plurality of rotary members.

Moreover, the plurality of rotary members are preferably provided from the distal side (e.g., a wrist side with respect to an upper arm) to the proximal side (e.g., a shoulder side with respect to the upper arm). Thus, even if the thickness of the arm to which the cuff is attached differs between the distal side and proximal side and the slide amount greatly differs between the distal side and proximal side, the rotary member on the distal side and the rotary member on the proximal side can have different rotation amounts. This further ensures that noise caused by friction can be reduced.

Preferably, the slide means is a rod member which is circular in section and which is provided in a direction perpendicular to a direction where the one end and the other end of the cuff slide.

Thus, the slide means can be simple in configuration, thereby enabling a reduction in manufacturing costs.

Preferably, the slide means is a low-friction sheet in contact with at least one of one end and the other of the cuff.

Thus, the slide means can be simple in configuration, thereby enabling a reduction in manufacturing costs.

BEST MODE FOR CARRYING OUT THE INVENTION

First Embodiment of Blood Pressure Monitor

A first embodiment of a blood pressure monitor of the present invention will be described below with reference to the drawings.

Figure 1:
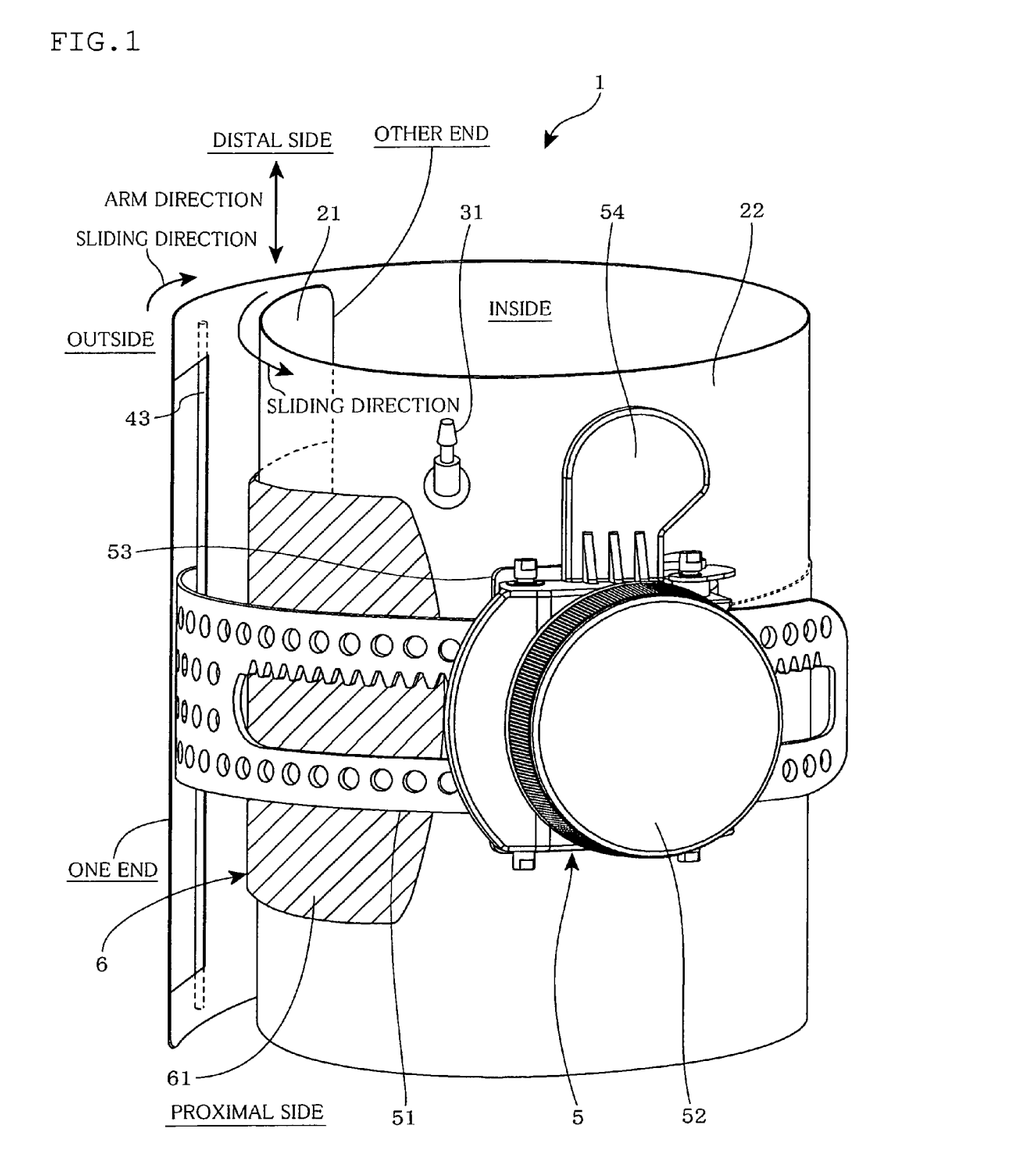
FIG. 1 shows a schematic perspective view of a cuff for use in a blood pressure monitor according to a first embodiment of the present invention.

FIG. 1 shows a schematic perspective view of a cuff for use in a blood pressure monitor according to the first embodiment of the present invention.

Figure 2:
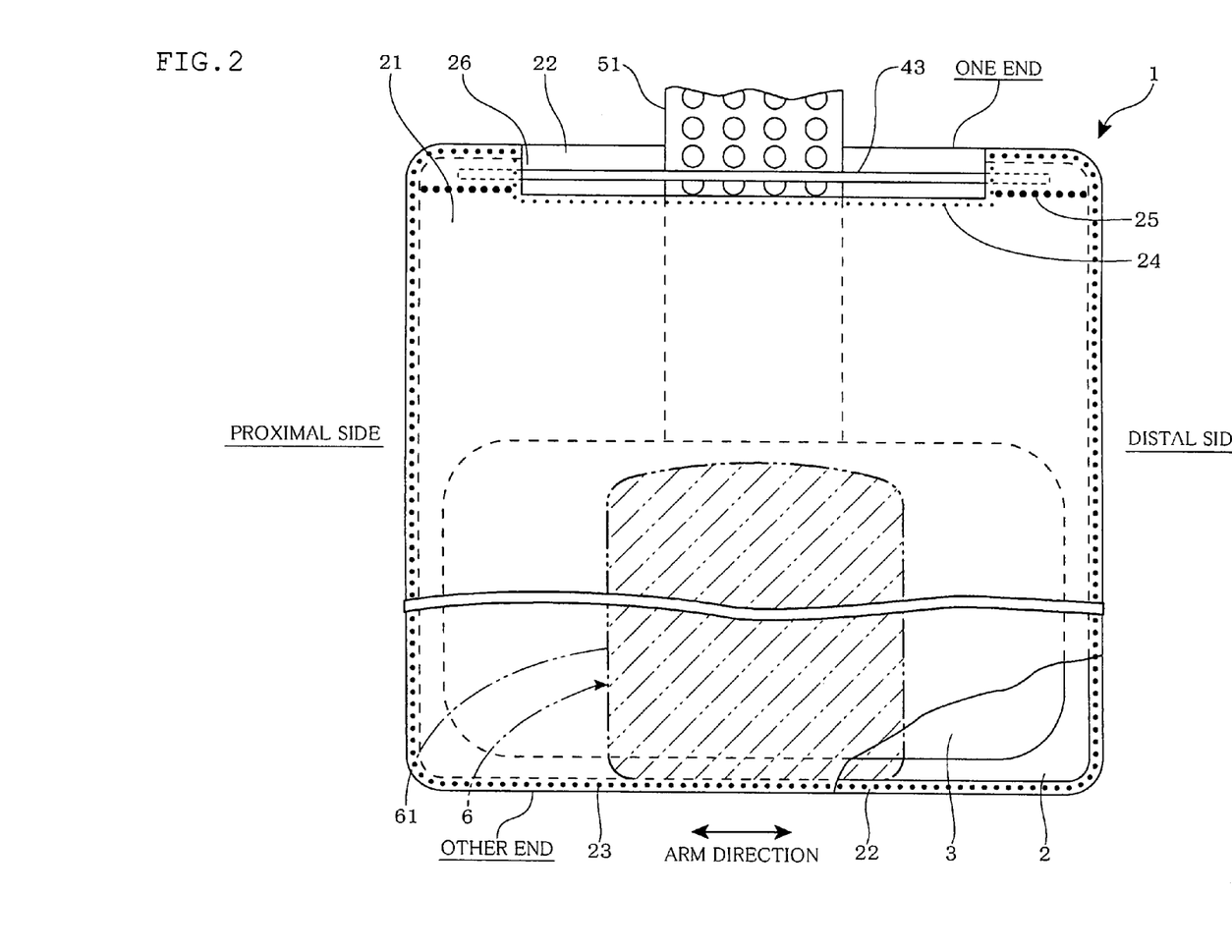
FIG. 2 shows a schematic expansion plan of essential parts of the cuff for use in the blood pressure monitor according to the first embodiment of the present invention.

FIG. 2 shows a schematic expansion plan of essential parts of the cuff for use in the blood pressure monitor according to the first embodiment of the present invention.

In FIGS. 1 and 2, a cuff 1 is a cuff that is used in an automatic blood pressure monitor. The cuff 1 includes a core 2, an air bag 3, fastening means 5, a cushion member 6 and the like. This cuff 1 is used in a rolled condition where one end of the cuff is wound within the other end thereof. Thus, an automatic blood pressure measurement is made.

In addition, the configuration for carrying out the automatic blood pressure measurement is substantially similar to the configuration of the above-described oscillometric electronic blood pressure monitor 100.

The air bag 3 has a rectangular shape, and is affixed to the inside of the core 2 by, for example, a double-sided tape (not shown). Moreover, the air bag 3 has, on its outer surface, a projecting joint 31 to be coupled to the above-mentioned tube 116 (see FIG. 5). This joint 31 is exposed outward through the core 2 and an outer cover 22. The air bag 3 is generally shaped to be longitudinally shorter than the core 2, and is provided on the side of the other end of the core 2.

In addition, the fixing of the air bag 3 is not limited to the above-mentioned configuration. For example, although not shown, sewing margins are provided in the outer peripheral parts of both longitudinal ends of the air bag 3, and the sewing margins provided in the air bag 3 and the core 2 are stitched together. The air bag 3 may be fixed to the core 2 in this manner.

The core 2 is a substantially rectangular sheet made of a resin, and is provided with the air bag 3 inside as described above. The core 2 to which the air bag 3 is affixed is stored in an inner cover 21 and the outer cover 22 so as to be interposed between the rectangular inner cover 21 covering the inner surface of the core 2 and the rectangular outer cover 22 covering the outer surface of the core 2. Resin cloth is generally used for the inner cover 21 and the outer cover 22. The inner cover 21 and the outer cover 22 are stitched together with a thread 23 on their outer edges except for a cutout 26 described below so as to interpose the core 2 and the air bag 3 therebetween.

As the cushion member 6 of the present embodiment, a raised fabric 61 like the loop surface of a hook-and-loop fastener, for example, is used. This raised fabric 61 is stitched onto the outer cover 22 over a relatively wide range from the other end of the cuff 1 to a position at where one end of the diametrically reduced cuff 1 arrives so as to be in contact with one end of the cuff 1 and others. That is, the raised fabric 61 is efficiently disposed at a place where there is great possibility of friction between one end and the other end of the cuff 1. Thus, the raised fabric 61 is disposed at a place where one end and the other end of the cuff 1 rub against each other, and absorbs, with its raised fibers, vibrations caused by the friction. This makes it possible to effectively prevent noise caused by the vibrations resulting from the friction.

In addition, the cushion member 6 is not exclusively provided at the above-mentioned place. For example, the cushion member 6 may be provided in the vicinity of the tip of one end of the cuff 1, or the cushion members 6 may be provided both in the vicinity of the tip of one end of the cuff 1 and in the vicinity of the tip of the other end of the cuff 1.

In addition, the kind, thickness, size, number and attachment place of the raised fabrics 61 can be freely selected.

Preferably, a rod member 43 may be provided at one end of the cuff 1. This rod member 43 is circular in section, and is provided in a direction perpendicular to a direction where one end and the other end of the cuff 1 slide. That is, the rod member 43 is in line contact with the other end side of the cuff 1, and reduces frictional resistance between one end and the other end side. Thus, one end and the other end side smoothly slide, so that noise caused by the friction can be inhibited. Such a rod member 43 enables a simpler configuration than slide means 4 in a second embodiment. This enables a reduction in manufacturing costs.

In addition, the direction where one end and the other end of the cuff 1 slide (abbreviated as the sliding direction when appropriate) means the direction where one end and the other end are circumferentially separated from each other. As shown in FIG. 1, a clockwise direction is the sliding direction for one end, while a counterclockwise direction is the sliding direction for the other end.

Furthermore, the rod member 43 is provided in the cutout 26 of the core 2 similarly to the slide means 4 in the second embodiment described later. That is, the rod member 43 is provided in the vicinity of the tip of one end of the cuff 1. Thus, the rod member 43 is efficiently disposed at a place where there is great possibility of friction between one end and the other end of the cuff 1.

In addition, the rod member 43 is not exclusively provided at the above-mentioned position. For example, the rod member 43 may be provided in the vicinity of the tip of the other end of the cuff 1, or the rod members 43 may be provided both in the vicinity of the tip of one end of the cuff 1 and in the vicinity of the tip of the other end of the cuff 1.

Furthermore, similarly to a shaft 42 in the second embodiment, the rod member 43 has its both ends stored between the core 2 and the outer cover 22 covering the core 2. In order to further ensure the positioning of both ends of the rod member 43, the outer cover 22, the core 2 and the inner cover 21 are stitched together with a thread 25 along the rod member 43 on the other end side at both ends of the rod member 43. Thus, both ends of the rod member 43 are easily held.

As described above, the raised fabric 61 is provided on the other end side of the cuff 1, and thus one end and the other end side of the cuff 1 slide via the rod member 43, so that vibrations caused by the friction can be further absorbed by the raised fabric 61. Owing to such composite effects, noise caused by the friction can be effectively inhibited.

In addition, the rod member 43 may be rotatably held or unrotatably held. Moreover, the rod member 43 is a relatively thin round rod, and its diametrical size can be freely selected. Further, the rod member 43 is preferably made of a metal in terms of strength, but may be made of a resin.

The fastening means 5 tightens the core 2, the air bag 3, etc. onto the upper arm and maintains the tightened state. The fastening means 5 includes a tightening belt 51, a knob 52, a base 53, a release lever 54 and the like.

The base 53 is attached to substantially the center of the core 2 by adhesive bonding, welding or the like. The tightening belt 51 has one end coupled to the base 53, and is stored between the core 2 and the outer cover 22 up to the one end side. Moreover, the other end of the tightening belt 51 projects outward from between the outer cover 22 and the rod member 43. At the other end of the tightening belt 51, a rack is engaged with a pinion (not shown) coupled to the knob 52.

When the knob 52 is turned clockwise, the tightening belt 51 of the fastening means 5 having the above-described configuration tightens the core 2, the air bag 3, etc. so as to reduce their diameters, and maintains the tightened state. Then, a blood pressure is measured. When the release lever 54 is pressed down, the tightening belt 51 releases the tightened state.

Now, the operation of the cushion member 6, etc. of the cuff 1 having the above-described configuration is described.

First, a subject to have his/her blood pressure measured inserts the arm into the cuff 1, and rotates the knob 52 when the cuff 1 has reached the upper arm. The tightening belt 51 lightly tightens the upper arm so as to reduce the core 2, the air bag 3, etc. in diameter. Then, when predetermined tightening force is reached, the knob 52 runs idle due to a torque limiter mechanism, and the tightened state is maintained.

Then, when air is sent into the air bag 3 from the joint 31 to which the tube 116 is connected, the air bag 3 compresses the arm. At this moment, the pressure sensor 113 in communication with the tube 116 detects a pressure signal containing a pulse wave as described above, and outputs the pressure signal to the information processing unit 120.

When air is further sent into the air bag 3, the air bag 3 compresses the arm by greater force. Due to the counteraction of this force, one end and the other end of the cuff 1 move a slight distance away from each other. At this point, even if one end of the cuff 1 slightly rubs against the other end thereof, vibrations caused by the friction are absorbed by the cushion member 6 made of the raised fabric 61. This makes it possible to effectively inhibit the noise caused by the vibrations resulting from the friction.

Moreover, one end and the other end of the cuff 1 slide without rubbing against each other owing to the rod member 43 provided in a direction perpendicular to the sliding direction. This makes it possible to more effectively inhibit the noise caused by the friction.

As described above, the cuff 1 can effectively inhibit the noise caused by the friction. This makes it possible to effectively prevent troubles as follows: for example, noise is erroneously detected as a pulse wave signal, and cuff pressure cannot be automatically set; or erroneous cuff pressure is set. Thus, an automatic blood pressure monitor with the cuff 1 is capable of significantly improving the reliability in the automatic elevation of the cuff pressure.

While the rod member 43 is provided in addition to the raised fabric 61 serving as the cushion member 6 in the present embodiment, the raised fabric 61 alone may be provided without providing the rod member 43. This also makes it possible to obtain substantially similar effects.

Second Embodiment of Blood Pressure Monitor

Figure 3:
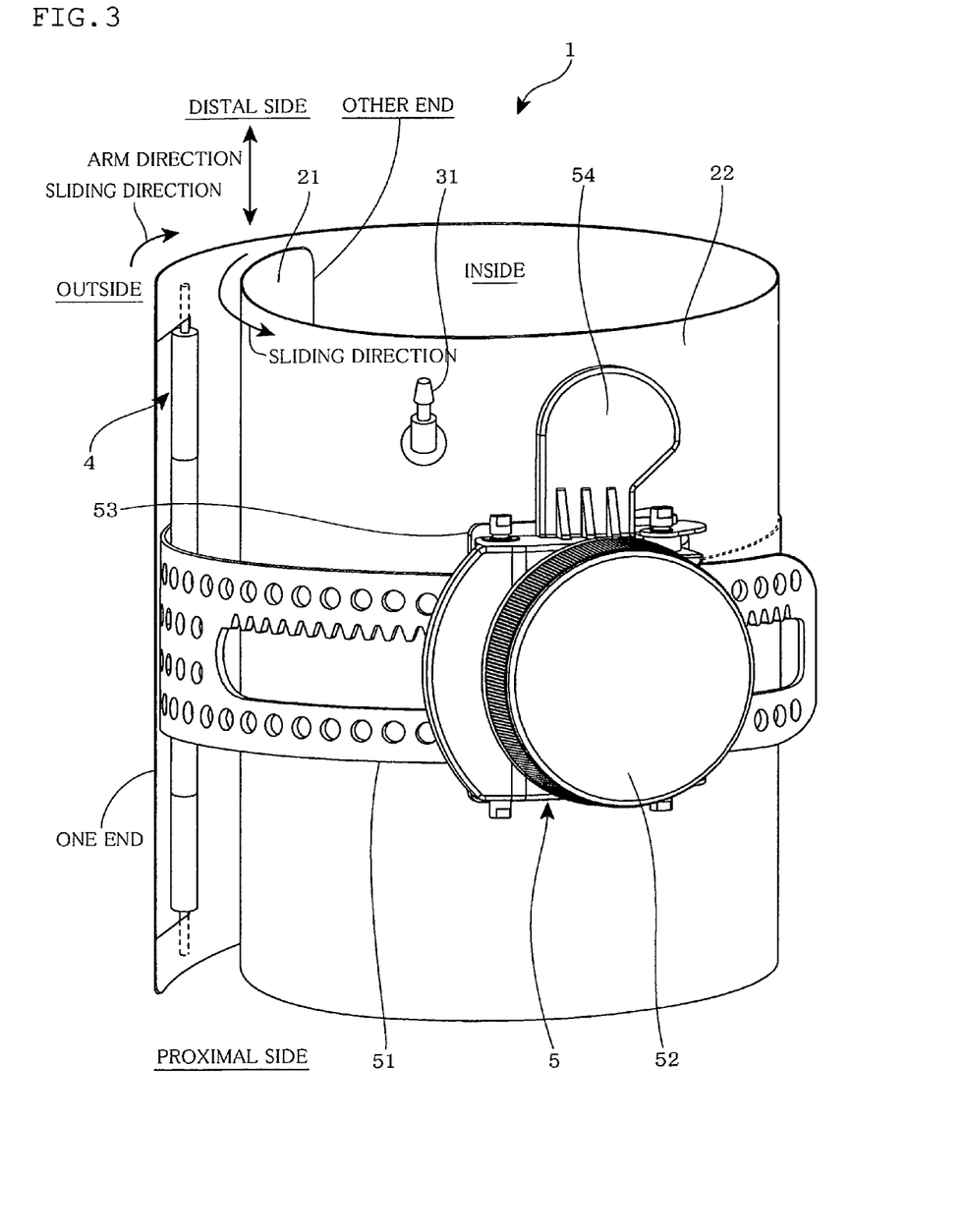
FIG. 3 shows a schematic perspective view of a cuff for use in a blood pressure monitor according to a second embodiment of the present invention.

The second embodiment of a blood pressure monitor of the present invention will be described below with reference to the drawings. FIG. 3 shows a schematic perspective view of a cuff for use in the blood pressure monitor according to the second embodiment of the present invention.

Figure 4:
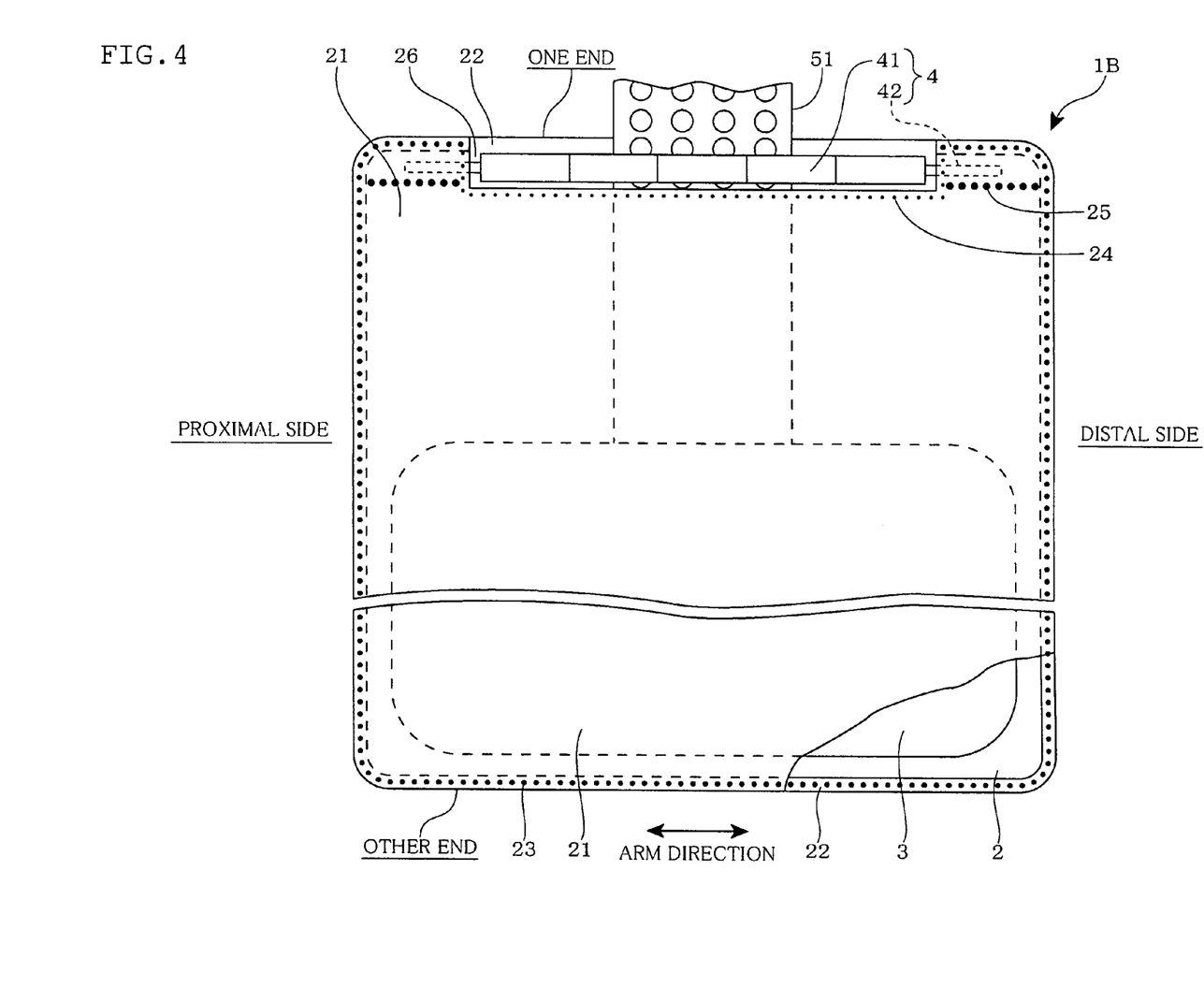
FIG. 4 shows a schematic expansion plan of essential parts of the cuff for use in the blood pressure monitor according to the second embodiment of the present invention.

FIG. 4 shows a schematic expansion plan of essential parts of the cuff for use in the blood pressure monitor according to the second embodiment of the present invention.

As shown in FIGS. 3 and 4, a cuff 1B used in the automatic blood pressure monitor in the second embodiment is different from that in the first embodiment in that the cuff 1B includes the slide means 4 instead of the cushion member 6. Therefore, components similar to the components in the first embodiment are provided with the same reference numbers and are not described in detail.

In addition, the configuration for carrying out the automatic blood pressure measurement is substantially similar to the configuration of the above-described oscillometric electronic blood pressure monitor 100.

In the cuff 1B of the present embodiment, a belt-shaped cutout 26 extending in the arm direction is formed substantially in the center of the tip of one end of a core 2. The slide means 4 is provided at the position of this cutout 26. That is, the slide means 4 is provided in the vicinity of the tip of one end of the cuff 1B. Thus, the slide means 4 is efficiently disposed at a place where there is great possibility of friction between one end and the other end of the cuff 1B. Moreover, a portion of an inner cover 21 is cut into about the same shape as the cutout 26, and this cut portion and the core 2 are stitched together with a thread 24.

In addition, the slide means 4 is not exclusively provided at the above-mentioned position. For example, the slide means 4 may be provided in the vicinity of the tip of the other end of the cuff 1B, or the slide means 4 may be provided both in the vicinity of the tip of one end of the cuff 1B and in the vicinity of the tip of the other end of the cuff 1B. Moreover, the slide means 4 may be provided between one end and the other end of the cuff 1B.

The slide means 4 has a cylindrical member 41 and a shaft 42. The cylindrical member 41 is made of a resin, and is a rotary member. The shaft 42 is made of steel, and is inserted into the cylindrical member 41.

Although not shown, a through-hole is formed in the cylindrical member 41 along its central axis. The shaft 42 is inserted into this through-hole. The shaft 42 is provided in a direction perpendicular to the sliding direction of one end and the other end of the cuff 1B. Thus, the cylindrical member 41 is in contact with an outer cover 22 on the other end side, and is rotatable in the direction where one end and the other end of the cuff 1B slide (abbreviated as the sliding direction when appropriate). In addition, the sliding direction means the direction where one end and the other end are circumferentially separated from each other. As shown in FIG. 3, a clockwise direction is the sliding direction for one end, while a counterclockwise direction is the sliding direction for the other end.

The slide means 4 can thus be simple in configuration by the use of the shaft 42. This enables a reduction in manufacturing costs.

Furthermore, both ends of the shaft 42 projecting from the cylindrical member 41 are stored between the core 2 and the outer cover 22 covering this core 2. In order to further ensure the positioning of both ends of the shaft 42, the outer cover 22, the core 2 and the inner cover 21 are stitched together with a thread 25 along the shaft 42 on the other end side at both ends of the rod member 43. Thus, both ends of the shaft 42 are easily held without providing any particular bearing.

The cylindrical member 41 is in line contact with the outer cover 22 on the other end side, and the contact area is reduced. Therefore, noise caused by friction is further reduced.

Although the cylindrical member 41 is provided as the rotary member in the present embodiment, the rotary member is not limited to the cylindrical member 41. For example, a spherical member or barrel-shaped member may be used instead. A combination of the cylindrical member 41 and the spherical member, etc. may be used. Moreover, the outside diameter of the cylindrical member 41 may be changed.

Furthermore, the slide means 4 includes five cylindrical members 41 on the shaft 42. The provision of a plurality of rotary members in this manner further ensures the reduction of noise caused by friction.

Moreover, the five cylindrical members 41 of the slide means 4 are arranged from the distal side to proximal side of the cuff 1B. Thus, even if the thickness of the arm to which the cuff 1B is attached differs between the distal side and proximal side and the slide amount greatly differs between the distal side and proximal side, the cylindrical member 41 on the distal side and the cylindrical member 41 on the proximal side can have different rotation amounts. This further ensures the reduction of noise caused by friction.

In addition, the number of the cylindrical members 41 is not limited to five, and may be, for example, three. Preferably, the number of the cylindrical members 41 is two or more. This makes it possible for the respective cylindrical members 41 to have different rotation amounts when the thickness of the arm differs between the distal side and proximal side as described above.

Now, the operation of the slide means 4 of the cuff 1B having the above-described configuration is described.

First, a subject to have his/her blood pressure measured inserts the arm into the cuff 1B, and rotates a knob 52 when the cuff 1B has reached the upper arm. The tightening belt 51 lightly tightens the upper arm so as to reduce the core 2, the air bag 3, etc. in diameter. Then, when predetermined tightening force is reached, the knob 52 runs idle due to a torque limiter mechanism, and the tightened state is maintained.

Then, when air is sent into the air bag 3 from a joint 31 to which a tube 116 is connected, the air bag 3 compresses the arm. At this moment, a pressure sensor 113 in communication with the tube 116 detects a pressure signal containing a pulse wave as described above, and outputs the pressure signal to an information processing unit 120.

When air is further sent into the air bag 3, the air bag 3 compresses the arm by greater force. Due to the counteraction of this force, one end and the other end of the cuff 1B move a slight distance away from each other. At this point, one end and the other end of the cuff 1B slide without rubbing against each other owing to the slide means 4 having the cylindrical member 41 which rotates in the sliding direction. This makes it possible to effectively inhibit the noise caused by friction.

As described above, the cuff 1B can effectively inhibit the noise caused by the friction. This makes it possible to effectively prevent troubles as follows: for example, noise is erroneously detected as a pulse wave signal, and cuff pressure cannot be automatically set; or erroneous cuff pressure is set. Thus, the automatic blood pressure monitor in the present embodiment is capable of significantly improving the reliability in the automatic elevation of the cuff pressure.

The preferred embodiments of the blood pressure monitor of the present invention have been illustrated above. However, it goes without saying that the blood pressure monitor according to the present invention is not exclusively limited to the embodiments described above, and various modifications can be made within the spirit of the present invention.

For example, the blood pressure monitor is not limited to the oscillometric electronic blood pressure monitor. The present invention can also be applied to, for example, an automatic blood pressure monitor which measures a blood pressure on the basis of Korotkoff sounds.

Moreover, the cuff includes the fastening means 5 with the tightening belt 51, but is not limited to this. The present invention can also be applied to a cuff which includes, for example, compressively fixing airbag instead of the fastening means 5.

While the cushion member 6 made of the raised fabric 61 is combined with the rod member 43 in the first embodiment, the present invention is not limited to this. For example, the cushion member 6 made of the raised fabric 61 may be combined with the slide means 4 in the second embodiment which has the rotary member 41 and the shaft 42. Moreover, the cushion member 6 made of the raised fabric 61 can also be provided independently in the cuff.

Furthermore, the slide means in the present invention is not limited to the slide means 4 shown in the embodiment described above. For example, a low-friction sheet in contact with at least one of one end and the other of the cuff can be used as the slide means. A release sheet coated with silicone is suitable for the low-friction sheet. In this case, manufacturing costs can be reduced by the use of the release sheet. In addition, the release sheet can be affixed at a position similar to the position of the raised fabric 61 in the first embodiment, and the affixing position, size, number and the like of the release sheets can be freely changed.

Still further, instead of the slide means 4 including the cylindrical member 41 and the shaft 42, the rod member 43 in the first embodiment may be used as the slide means.

INDUSTRIAL APPLICABILITY

As described above, the cuff used in the blood pressure monitor of the present invention is not exclusively used in a blood pressure monitor cuff. For example, the present invention can also be effectively applied to a stanching cuff which requires an accurate measurement of a pulse wave during pressure elevation.

The invention claimed is:
1. A blood pressure monitor to measure a blood pressure, comprising:
  a cuff having an inner cover, an outer cover, and a core;
  a cushion member present on the outer cover; and
  a tightening unit including a tightening belt and holding an end of the cuff rolled into other end of the cuff such that the tightening member keeps the cuff in a cylindrical shape,
  wherein the cushion member is present where the inner cover at the end of the cuff rubs against the outer cover at the other end of the cuff,
  an end of the tightening belt is connected to a base attached to a center of the core,
  a center part of the tightening belt is stored between the inner cover and the outer cover while the center part of the tightening belt is sandwiched between the core and the outer cover,
  other end of the tightening belt outwardly protrudes from between the inner cover and the outer cover, and
  the cushion member extends long enough that even when diametrically reduced, the cushion member remains between the overlapping ends of the cuff.
2. The blood pressure monitor according to claim 1, wherein the cushion member is a loop surface of a hook-and-loop fastener.
3. The blood pressure monitor according to claim 1, wherein the cushion member is present on the inner cover and the outer cover.
4. A blood pressure monitor to measure a blood pressure, comprising:
  a cuff having an inner cover, an outer cover and a core;
  a slider present on the inner cover; and
  a tightening unit including a tightening belt and holding an end of the cuff rolled into other end of the cuff such that the tightening member keeps the cuff in a cylindrical shape,
  wherein the slider is present where the inner cover at the end of the cuff rubs against the outer cover at the other end of the cuff,
  the slider has at least one rotary member which is in contact with at least one of the end of the cuff or the other end of the cuff and which is rotatable in a direction where the end of the cuff and the other end of the cuff slide, and a shaft present in a direction perpendicular to the direction where the end of the cuff and the other end of the cuff slide and inserted into a through-hole formed in the rotary member, and wherein an end of the tightening belt is connected to a base attached to a center of the core, a center part of the tightening belt is stored between the inner cover and the outer cover while the center part of the tightening belt is sandwiched between the core and the outer cover, and other end of the tightening belt outwardly protrudes from between the inner cover and the outer cover.

5. The blood pressure monitor according to claim 4, wherein the rotary member is a cylindrical member and/or a spherical member.

6. The blood pressure monitor according to claim 4, wherein the slider is a rod member which is circular in a section thereof and which is provided in a direction perpendicular to a direction where the end of the cuff and the other end of the cuff slide.

7. The blood pressure monitor according to claim 6, wherein the core and the inner cover has a cutout, the rod member is present in the cutout in a vicinity of the other end of the cuff, an end of the rod member and other end of the rod member are stored between the core and the outer cover which covers the core, and the tightening belt is present between the outer cover and the rod member.

8. The blood pressure monitor according to claim 4, wherein the core and the inner cover has a cutout, the shaft is present in the cutout in a vicinity of the other end of the cuff, an end of the shaft and other end of the shaft are stored between the core and the outer cover which covers the core, and the tightening belt is present between the outer cover and the rotary member.

9. A blood pressure monitor to measure a blood pressure, comprising:

a cuff having an inner cover and an outer cover;

a slider present on the inner cover or the outer cover; and a tightening unit including a tightening belt and holding an end of the cuff rolled into other end of the cuff such that the tightening member keeps the cuff in a cylindrical shape, wherein the slider is present where the inner cover at the end of the cuff rubs against the outer cover at the other end of the cuff, and the slider is a release sheet coated with silicone.

10. A blood pressure monitor to measure a blood pressure, comprising:

a cuff having an inner cover, an outer cover and a core;

a slider present on the inner cover or the outer cover; and a tightening unit including a tightening belt and holding an end of the cuff rolled into other end of the cuff such that the tightening member keeps the cuff in a cylindrical shape, wherein the slider is present where the inner cover at the end of the cuff rubs against the outer cover at the other end of the cuff, the slider is a rod member which is circular in a section thereof and which is provided in a direction perpendicular to a direction where the end of the cuff and the other end of the cuff slide, an end of the tightening belt is connected to a base attached to a center of the core, a center part of the tightening belt is stored in the inner cover and the outer cover while the center part of the tightening belt is sandwiched between the core and the outer cover, and other end of the tightening belt outwardly protrudes from the inner cover and the outer cover.

* * * * *